United States Patent
Bransby et al.

(10) Patent No.: US 11,339,364 B2
(45) Date of Patent: May 24, 2022

(54) MICRO ALTERNATING TANGENTIAL FLOW PERFUSION FILTER, MICRO BIOREACTOR, AND METHODS OF USE THEREOF

(71) Applicant: Repligen Corporation, Waltham, MA (US)

(72) Inventors: Michael Bransby, Waltham, MA (US); Philip Yuen, Waltham, MA (US)

(73) Assignee: Repligen Corporation, Waltham, MA (US)

( * ) Notice: Subject to any disclaimer, the term of this patent is extended or adjusted under 35 U.S.C. 154(b) by 24 days.

(21) Appl. No.: 16/171,867

(22) Filed: Oct. 26, 2018

(65) Prior Publication Data
US 2019/0127678 A1    May 2, 2019

Related U.S. Application Data

(60) Provisional application No. 62/577,436, filed on Oct. 26, 2017.

(51) Int. Cl.
*B01D 61/14* (2006.01)
*B01D 61/18* (2006.01)
(Continued)

(52) U.S. Cl.
CPC ............ *C12M 29/10* (2013.01); *B01D 61/147* (2013.01); *B01D 61/18* (2013.01); *C12M 29/04* (2013.01);
(Continued)

(58) Field of Classification Search
CPC ............ B01D 2311/16; B01D 2315/10; B01D 61/142; B01D 61/147; B01D 61/18; C12M 29/04; C12M 29/10; C12M 33/14
See application file for complete search history.

(56) References Cited

U.S. PATENT DOCUMENTS

2008/0281200 A1   11/2008   Voic et al.
2010/0112690 A1   5/2010    Eddington
(Continued)

FOREIGN PATENT DOCUMENTS

| JP | 2015530110 A1 | 10/2015 |
| WO | 2012026978 A2 | 3/2012 |
| WO | WO2017082990 A1 | 5/2017 |

OTHER PUBLICATIONS

Cunha et al.; Exploring continuous and integrated strategies for the up- anddownstream processing of human mesenchymal stem cells, Journal of Biotechnology 213 (2015) 97-108. (Year: 2015).*

(Continued)

*Primary Examiner* — Pranav N Patel
(74) *Attorney, Agent, or Firm* — KDB

(57) ABSTRACT

A micro alternating tangential flow (microATF) perfusion filter includes a hollow cylinder having a proximal end and a distal end. The proximal end is connected in series to a permeate chamber, followed by a retentate chamber. The proximal end either (i) terminates in or at the permeate chamber, or (ii) terminates in or at the retentate chamber. The portion of the proximal end within the permeate chamber, in a case of (ii), possesses at least one opening allowing fluid communication between an inside of the hollow cylinder and the permeate chamber. The microATF perfusion filter further includes an inlet, positioned over the retentate chamber, for communication with a source of positive or negative pressure, and an outlet, positioned in a wall of the permeate chamber, which can be connected to a check valve, which, in turn, can be connected to a hydrophobic fluid vent filter.

16 Claims, 5 Drawing Sheets

(51) Int. Cl.
*C12M 1/00* (2006.01)
*C12M 1/26* (2006.01)

(52) U.S. Cl.
CPC ........... *C12M 33/14* (2013.01); *B01D 61/142* (2013.01); *B01D 2311/16* (2013.01); *B01D 2315/10* (2013.01)

(56) References Cited

U.S. PATENT DOCUMENTS

| | | | | |
|---|---|---|---|---|
| 2012/0258459 | A1* | 10/2012 | Huang | B01L 3/5021 |
| | | | | 435/6.11 |
| 2014/0011270 | A1 | 1/2014 | Chotteau et al. | |
| 2014/0154745 | A1* | 6/2014 | Zijlstra | C12P 21/005 |
| | | | | 435/69.6 |
| 2014/0287509 | A1* | 9/2014 | Sharei | C12M 23/16 |
| | | | | 435/455 |
| 2015/0079194 | A1* | 3/2015 | Hanna | B01D 69/02 |
| | | | | 424/530 |
| 2015/0247114 | A1 | 9/2015 | Gebauer | |
| 2017/0122845 | A1* | 5/2017 | Logue | B01D 15/02 |
| 2017/0292103 | A1* | 10/2017 | Cattaneo | C12M 25/10 |

OTHER PUBLICATIONS

Thesis for obtaining the degree of Master of Science in the Pharmaceutical Biotechnology Course by Nicolas Marx, Hamburg University of Applied Sciences, 109 pages, Jan. 25, 2015. (Year: 2015).*

International Search Report and Written Opinion dated Jan. 15, 2019 for PCT/US2018/057721 filed Oct. 26, 2018.

Supplementary European Search Report dated Dec. 7, 2020 for European Patent Application 18871613.8.

* cited by examiner

506

MICRO ALTERNATING TANGENTIAL FLOW PERFUSION FILTER, MICRO BIOREACTOR, AND METHODS OF USE THEREOF

This application claims the benefit of priority under 35 U.S.C. § 119(e) to U.S. Provisional Patent Application No. 62/577,436, filed Oct. 26, 2017, entitled "Micro Alternating Tangential Flow Perfusion Filter, Micro Bioreactor, And Methods Of Use Thereof," which application is incorporated herein by reference in its entirety.

FIELD

The present application relates generally to micro alternating tangential flow (microATF) perfusion filters, and more particularly, to apparatuses, systems and methods for use of the same.

BACKGROUND

Filtration is typically performed to separate, clarify, modify and/or concentrate a fluid solution, mixture or suspension. In the biotechnology and pharmaceutical industries, filtration is vital for the successful production, processing, and testing of new drugs, diagnostics and other biological products. For example, in the process of manufacturing biologicals, using animal cell culture, filtration is done for clarification, selective removal and concentration of certain constituents from the culture media or to modify the media prior to further processing. Filtration may also be used to enhances productivity by maintaining a culture in perfusion at high cell concentration. A wide variety of filtration systems exist that are adapted to large-scale filtration of media across various applications. However, conventional systems generally are ill-suited to filtering minute amounts of media in microscale implementations. Further, to accomplish concentration and/or sampling of small amounts of media, or perfusion of cells in cell culture media, conventional systems often have complicated structures that are difficult to manufacture and maintain, or are ill-suited for application to small volumes (e.g., micro bioreactors holding 30 mL of fluid or less, 20 mL of fluid or less, sometimes 15 mL of fluid or less). Those of ordinary skill in the art have resorted to the use of centrifuges to process such small volumes.

However, centrifuges cannot be used as a substitute for validation of commercial filtration processes, particularly in highly regulated fields such as biotechnology. Conventional bioprocessing vessels generally have a lower volume limit of approximately 1 L. The comparatively high volumes required by existing filtration vessels necessitates correspondingly high quantities of materials, and dedicated personnel. For smaller companies seeking to commercialize biotechnology products, the costs associated with existing processes may become prohibitive. By lowering the volumes required for effective filtration, a significant impact may be made in the overall cost of small-scale filtration processes while preserving the comparability of the data produced by such processes to larger scale processes.

SUMMARY

The present application discloses a micro alternating tangential flow (microATF) perfusion filter which includes a hollow cylinder having a proximal end and a distal end. The microATF perfusion filter may also be referred to as a μATF perfusion filter. The proximal end is connected in series to a permeate chamber, followed by a retentate chamber. The proximal end either (i) terminates in or at the permeate chamber, or (ii) terminates in or at the retentate chamber. The portion of the proximal end within the permeate chamber, in a case of (ii), possesses at least one opening allowing fluid communication between an inside of the hollow cylinder and the permeate chamber. The microATF perfusion filter further includes an inlet positioned over the retentate chamber, for communication with a source of positive or negative pressure, and an outlet, positioned in a wall of the permeate chamber, which can be connected to a check valve, which, in turn, can be connected to a hydrophobic fluid vent filter.

The present application discloses a system comprising a housing capable of holding a volume of cells in cell culture media of about 15 mL or less, a microATF and a fluid conduit between a well of the housing and the microATF. The microATF comprises (a) a hollow cylinder having a proximal end and a distal end, said proximal end being connected to (i) a permeate chamber, and (ii) a retentate chamber separated from the permeate chamber by a filter element; (b) an inlet, positioned over the retentate chamber, for communication with a source of alternating positive or negative pressure; (c) an outlet, positioned in a wall of the permeate chamber. In some embodiments, the housing is a multi-well plate with a capacity of 0.2 ml, 0.5 mL, 1.0 mL, 2.0 mL, 5.0 mL, 10 mL, or 15 mL. In some embodiments, the outlet is capped with a check valve that allows fluid to flow through the filter into the permeate chamber while preventing backflow through the filter into the retentate chamber.

The present application further discloses a process vessel for perfusing cells in cell culture media. The process vessel comprises a housing capable of holding a volume of cells in cell culture media of about 15 mL or less. The housing of the bioreactor is equipped, via an opening or a connector, with a micro alternating tangential perfusion filter comprising: (a) a hollow cylinder having a proximal end and a distal end, said proximal end being connected in series to a permeate chamber, followed by a retentate chamber; (b) an inlet, positioned over the retentate chamber, for communication with a source of positive or negative pressure; and (c) an outlet, positioned in a wall of the permeate chamber.

The present application also discloses a method of conducting a discontinuous perfusion of cells in cell culture media across an alternating tangential flow perfusion filter. The method comprises withdrawing cells in cell culture media ranging in volume from about 0.5 mL to about 5 mL through a lumen of one or more hollow fiber filters past a permeate chamber and into a retentate chamber. The method further comprises returning said cells in cell culture media through the lumen of said one or more hollow fiber filters, whereby a volume of cell culture media passes across a porous wall of said one or more hollow fiber filters and collects in said permeate chamber.

The present application additionally discloses a method of perfusing cells in cell culture media held in a process vessel, which holds no more than about 15 mL of cells in culture media. The method comprises withdrawing cells in cell culture media from a process vessel comprising a housing holding the cells in cell culture media using a microATF filter comprising one or more hollow fiber filters, a permeate chamber equipped with an outlet, a retentate chamber and an inlet for connecting the microATF filter to a source of positive or negative pressure. The method further comprises returning the cells in cell culture media to the process vessel.

The disclosed embodiments may be modified and employed in various ways. For example, various configurations are readily apparent, including a system in which a plurality of process vessels may be provided. Alternative exemplary embodiments relate to other features and combinations of features as may be recited in the claims.

BRIEF DESCRIPTION OF THE DRAWINGS

The disclosure will become more fully understood from the following detailed description, taken in conjunction with the accompanying figures, wherein like reference numerals, symbols or terms generally identify similar components, unless context dictates otherwise, and in which.

DESCRIPTION OF SELECTED EMBODIMENTS

Figure 1:
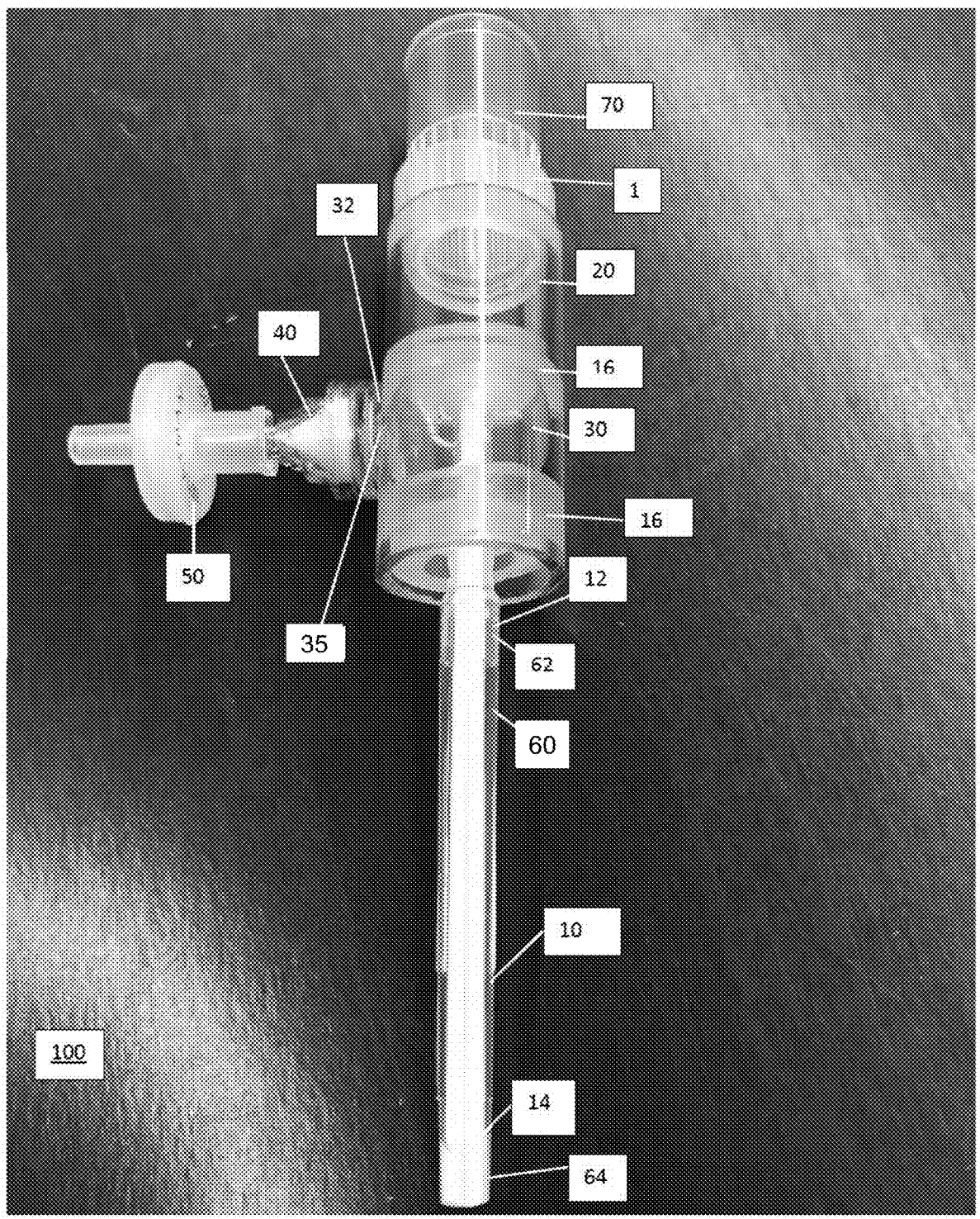
FIG. 1 depicts a micro alternating tangential flow (microATF) perfusion filter device according to an exemplary embodiment.

An embodiment relates to a microATF perfusion filter including a hollow cylinder having a proximal end and a distal end. The proximal end is connected in series to a permeate chamber, followed by a retentate chamber. The proximal end either (i) terminates in or at the permeate chamber, or (ii) terminates in or at the retentate chamber. The portion of the proximal end within the permeate chamber, in a case of (ii), possesses at least one opening allowing fluid communication between an inside of the hollow cylinder and the permeate chamber. The microATF perfusion filter further includes an inlet, positioned over the retentate chamber, for communication with a source of positive or negative pressure, and an outlet, positioned in a wall of the permeate chamber, which can be connected to a check valve, which, in turn, can be connected to a hydrophobic fluid vent filter.

In an embodiment of a microATF perfusion filter, the outlet is capped with a check valve that allows gas to escape from the permeate chamber while allowing no gas to enter.

In an embodiment of a microATF perfusion filter, the proximal end terminates in or at the permeate chamber.

In an embodiment of a microATF perfusion filter, the perfusion filter further comprises one or more hollow fiber filters each having a first end and a second end, the one or more hollow fiber filters arranged longitudinally inside the hollow cylinder with the first end extending in a direction of the distal end of the hollow cylinder and the second end terminating in or at the retentate chamber.

In an embodiment of a microATF perfusion filter, the first end of the one or more hollow fiber filters extends down a length of the hollow cylinder and terminates at or near the distal end of the hollow cylinder.

In an embodiment of a microATF perfusion filter, the one or more hollow fiber filters have an inside diameter ranging from about 0.5 mm to about 1 mm.

In an embodiment of a microATF perfusion filter, the one or more hollow fiber filters comprises hollow fiber filter media having an average pore size ranging from about 0.2 μm to about 2.0 μm.

In an embodiment of a microATF perfusion filter, the one or more hollow fiber filters have an average pore size of about 0.65 μm.

In an embodiment of a microATF perfusion filter, the one or more hollow fiber filters have an average pore size that does not permit passage of molecules having a molecular weight ranging from about 20 kDa to about 70 kDa.

In an embodiment of a microATF perfusion filter, the one or more hollow fiber filters have an average pore size that does not permit passage of molecules having a molecular weight of about 30 kDa or more.

In an embodiment of a microATF perfusion filter, the one or more hollow fiber filters have an average pore size that does not permit passage of molecules having a molecular weight of about 50 kDa or more.

Another embodiment relates to a system for perfusing cells in cell culture media. The system comprises a housing capable of holding a volume of cells in cell culture media of about 15 mL or less. The system is equipped, via an opening or a connector, with a micro alternating tangential perfusion filter comprising: (a) a hollow cylinder having a proximal end and a distal end, said proximal end being connected to (i) a permeate chamber, and (ii) a retentate chamber separated from the permeate chamber by a filter element; (b) an inlet, positioned over the retentate chamber, for communication with a source of alternating positive or negative pressure; (c) an outlet, positioned in a wall of the permeate chamber. In another embodiment, a fluid conduit connects at least one well of the housings with the proximal end of the microATF. In another embodiment, the housing is a multi-well plate.

In an embodiment of a system, at least the distal end of the hollow cylinder is in contact with a volume of cells in cell culture media that might be held in the multi-well plate. In another embodiment, the multi-well plate has a capacity of 0.2 ml, 0.5 mL, 1.0 mL, 2.0 mL, 5.0 mL, 10 mL, or 15 mL.

In an embodiment of a system equipped with a perfusion filter, the filter outlet is capped with a check valve that allows fluid to flow through the filter into the permeate chamber while preventing backflow through the filter into the retentate chamber.

In an embodiment of a system equipped with a perfusion filter, the outlet allows for the removal, if desired, of cell culture media that might be deposited into the permeate chamber.

In an embodiment of a system, the filter element comprises a tubular membrane or at least one hollow fiber membrane. In an embodiment of a system, the filter element is characterized by a filter flux of 50-100 μl per cycle. In an embodiment of a system, the housing holds about 10 mL or less of a volume of cells in cell culture media. In an embodiment of a system, the housing holds about 5 mL or less of a volume of cells in cell culture media. In an embodiment of a system, the housing holds about 2 mL or less of a volume of cells in cell culture media. In an embodiment of a system, the housing holds about 1 mL or less of a volume of cells in cell culture media. In an embodiment of a system, the housing holds about 0.5 mL or less of a volume of cells in cell culture media. In an embodiment of a system, the housing holds about 0.2 mL or less of a volume of cells in cell culture media.

In an embodiment of a system equipped with a perfusion filter, the check valve of the perfusion filter is connected to a hydrophobic fluid vent filter.

In an embodiment of a system equipped with a perfusion filter, cells in cell culture media are withdrawn from the housing into the retentate chamber, when the inlet communicates with a source of negative pressure.

In an embodiment of a system equipped with a perfusion filter, said cells in cell culture media are returned to the housing, when the inlet communicates with a source of positive pressure, whereby a volume of cell culture media is deposited into the permeate chamber.

In an embodiment of a system, the system comprises plurality of fluid conduits connecting a plurality of wells of the multi-well plate with a plurality of microATFs.

In an embodiment of a system, the source of positive or negative pressure is provided through a pipette. In an embodiment of a system, the source of positive or negative pressure is provided through a pipette operated manually. In an embodiment of a system, the source of positive or negative pressure is provided through a pipette operated robotically.

In an embodiment of a system equipped with a perfusion filter, the volume of cell culture media deposited into the permeate chamber ranges from about 50 µL to about 500 µL.

In an embodiment of a system equipped with a perfusion filter, the volume of cell culture media deposited into the permeate chamber ranges from about 100 µL to about 300 µL.

Yet a further embodiment relates to a method of conducting a discontinuous perfusion of cells in cell culture media across an alternating tangential flow perfusion filter. The method comprises withdrawing cells in cell culture media ranging in volume from about 0.5 mL to about 5 mL through a lumen of one or more hollow fiber filters past a permeate chamber and into a retentate chamber. The method further comprises returning said cells in cell culture media through the lumen of said one or more hollow fiber filters, whereby a volume of cell culture media passes across a porous wall of said one or more hollow fiber filters and collects in said permeate chamber.

In an embodiment of a method of conducting a discontinuous perfusion, the volume of cell culture media, which collects in said permeate chamber, ranges from about 25 µL to about 1000 µL.

In an embodiment of a method of conducting a discontinuous perfusion, the volume of cell culture media, which collects in said permeate chamber, ranges from about 0.1 mL to about 0.5 mL.

In an embodiment of a method of conducting a discontinuous perfusion, the permeate chamber is equipped with an outlet that is capped with a check valve.

An additional embodiment relates to a method of perfusing cells in cell culture media held in a process vessel, which holds no more than about 15 mL of cells in culture media. The method comprises withdrawing cells in cell culture media from a process vessel comprising a housing holding the cells in cell culture media using a microATF filter comprising one or more hollow fiber filters, a permeate chamber equipped with an outlet, a retentate chamber and an inlet for connecting the microATF filter to a source of positive or negative pressure. The method further comprises returning the cells in cell culture media to the process vessel.

In an embodiment of a method of perfusing cells, a volume of cell culture media is deposited into the permeate chamber when returning the cells in cell culture media to the process vessel.

In an embodiment of a method of perfusing cells, cells in cell culture media withdrawn from the process vessel ranges in volume from about 0.5 mL to about 5 mL.

In an embodiment of a method of perfusing cells, the cells in cell culture media withdrawn from the process vessel ranges in volume from about 1.0 mL to about 3.0 mL.

In an embodiment of a method of perfusing cells, the cells in cell culture media withdrawn from the process vessel amount to about 2.0 mL in volume.

In an embodiment of a method of perfusing cells, the volume of cell culture media, which is deposited into the permeate chamber, ranges from about 10 µL to about 300 µL.

In an embodiment of a method of perfusing cells, the volume of cell culture media, which is deposited into the permeate chamber, ranges from about 50 µL to about 250 µL.

In an embodiment of a method of perfusing cells, the volume of cells in cell culture media, which is deposited into the permeate chamber, ranges from about 50 µL to 100 µL, or 100 µL to about 200 µL.

In an embodiment of a method of perfusing cells, the cells in cell culture media are withdrawn and returned over multiple cycles of alternating tangential flow of cells in cell culture media over a porous wall of said one or more hollow fiber filters. A filter flux, defined as the volume of fluid that passes through the filter from the feed/retentate channel to the permeate channel ranges from about 50 µL to 100 µL, or 100 µL to about 200 µL. Filter flux in this disclosure is defined as the flux that occurs during one alternating flow cycle.

In an embodiment of a method of perfusing cells, the withdrawal and return of cells in cell culture media over multiple cycles of alternating tangential flow are repeated intermittently.

In an embodiment of a method of perfusing cells, the withdrawal and return of cells in cell culture media over multiple cycles of alternating tangential flow are under a pressure of about 1 psi.

In an embodiment of a method of perfusing cells, the method further includes introducing fresh cell culture media to the process vessel.

In an embodiment of a method of perfusing cells, the fresh cell culture media introduced amounts to approximately the volume of cell culture media, which is deposited into the permeate chamber over said multiple cycles of alternating tangential flow.

In an embodiment of a method of perfusing cells, about 1 mL to about 3 mL of fresh cell culture media is introduced.

In an embodiment of a method of perfusing cells, about 1.5 mL to about 2.5 mL of fresh cell culture media is introduced.

In an embodiment of a method of perfusing cells, approximately 2 mL of fresh cell culture media is introduced.

An additional embodiment relates to a method of method of harvesting a cell product from a cell culture. The method comprises culturing cells in a starting volume of 15 ml or less of a culture medium until the cells have produced a cell product at a harvest concentration in the culture medium, wherein the cells are cultured in a cell culture system including a process vessel connected to a micro-alternating tangential flow (microATF) device, transferring the culture medium between the process vessel and the microATF device by causing an alternating flow of the culture medium therebetween, wherein the alternating flow causes a fluid containing the cell product to pass through the microATF device and into a permeate chamber and reduces a concentration of cell product in the culture medium below the harvest concentration, and extracting the liquid containing cell product from the permeate chamber.

In an embodiment, the method of harvesting a cell product from a cell culture further comprises refilling the process vessel with a fluid to a desired volume; and repeating the steps of the method.

In an embodiment of the method of harvesting a cell product from a cell culture, the process vessel is a multi-well plate.

In an embodiment of the method of harvesting a cell product from a cell culture, the starting volume is 0.2, 0.5, 1.0, 1.5, 2.0 mL.

In an embodiment of the method of harvesting a cell product from a cell culture, a plurality of fluid conduits connect a plurality of wells of the multi-well plate with a plurality of microATFs.

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of refereeing individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless otherwise indicated, all numbers expressing quantities of properties, parameters, conditions, and so forth, used in the specification and claims are to be understood as being modified in all instances by the term "about." Accordingly, unless indicated to the contrary, the numerical parameters set forth in the following specification and attached claims are approximations. Any numerical parameter should at least be construed in light of the number reported significant digits and by applying ordinary rounding techniques. The term "about" when used before a numerical designation, e.g., temperature, time, amount, and concentration including range, indicates approximations which may vary by (+) or (−) 10%, 5% or 1%.

As will be understood by one of skill in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

Filtration of biological fluids may be performed to separate blood into blood cells and plasma, among other implementations. For biomedical applications, it is important to be able to effectively carry out filtration so as to obtain precise amounts of desired material.

Alternating tangential flows of fluid may be used to perform filtering. More particularly, by alternating a tangential flow of fluid through a filter element, continuous filtration may be achieved. An alternating tangential flow system is described, for example, in U.S. Pat. No. 6,544,424 to Shevitz, the entire contents of which are incorporated herein for the background, apparatuses and technical content therein. Generally, alternating tangential flow filtration (ATF) includes passing a fluid, such as a cell culture medium, across a membrane or other permeable structure in alternating directions. A portion of the volume of the fluid, comprising one or more components that are suspended or solved therewithin, passes through the membrane, creating a filtrate or permeate (which terms are used interchangeably here) in which one or more the suspended or solved components is present in a higher concentration than in the original fluid. The portion of the fluid volume that does not pass through the filter is referred to as the retentate, and the space comprising the retentate, and defined in part by the membrane, is referred to as the feed channel and/or the retentate chamber. The space on the opposite side of the membrane is referred to as the permeate or filtrate chamber.

Alternating flows across the membrane are generated by the alternating application of positive and negative pressure to a portion of the feed channel. Alternating pressure may be provided using any suitable means, including, without limitation, by a reversible pump such as a diaphragm pump, or a piston or plunger pump. Other pumps may include peristaltic or magnetic pumps that are reversible. Those of skill in the art will appreciate that suitable pump structures may be elements of other devices that are not dedicated to pumping or filtration. These other devices may include, without limitation, pipettors (also referred to as pipettes) and syringes, and may be actuated manually by a user, or automatically. These aspects of the disclosure are discussed in greater detail below.

Filtration may be performed for purification, selective removal of unwanted constituents, and/or for maintaining or perfusing cells in cell culture media at a high cell concentration. Various types of filters may be used, including hollow fiber filters containing a plurality of hollow fibers bundled together. Filtrating using the aforementioned alternating tangential flow may be carried out, for example, by larger-scale equipment such as pumps and centrifuges. Such systems typically involve many components in complicated assemblies, which are difficult to maintain. The embodiments of the present disclosure, on the other hand, permit concentration of small volumes of cell culture media, perfusion of cells in cell culture media and/or sampling of the cell culture media without the use of centrifugation, among other benefits, as described in more detail below.

FIG. 1 depicts a micro alternating tangential flow (microATF) perfusion filter device 100. The microATF perfusion filter 100 includes a hollow cylinder 10 having a proximal end 12 and a distal end 14. The hollow cylinder 10 may be formed of a polymeric material. The hollow cylinder 10 is constructed so as to have a substantially uniform diameter, in at least one embodiment. In another embodiment, the hollow cylinder 10 is constructed so as to taper from the proximal end 12 to the distal end 14, such that a diameter at the distal end 14 is smaller than that at the proximal end 12. The proximal end 12 is connected, directly and/or indirectly, to other components of the microATF perfusion filter 100, as discussed in more detail below.

Referring again to the hollow cylinder 10, as shown in FIG. 1, the hollow cylinder 10 is arranged such that the proximal end 12 thereof is connected in series to a permeate chamber 30, followed by a retentate chamber 20. The proximal end 12 either (i) terminates in or at the permeate chamber 30, or (ii) terminates in or at the retentate chamber 20. The permeate chamber 30 is configured to receive filtrate generally containing liquid and relatively lower molecular weight solutes, whereas the retentate chamber 20 is configured to receive suspended solids and solutes of relatively higher molecular weight. As shown in FIG. 1, the permeate chamber 30 and retentate chamber 20 are arranged with the hollow cylinder 10 such that the proximal end 12 of the hollow cylinder, the permeate chamber 30, and the retentate chamber 20 are provided in a linear order of the proximal end 12, the permeate chamber 30, and the retentate chamber 20. Additionally, the hollow cylinder 10 is arranged with the permeate chamber 30 and the retentate chamber 20 such that a central axis of the hollow cylinder 10 aligns with a central axis of the permeate chamber 30 and a central axis of the retentate chamber 20.

Further, a portion or all of the proximal end 12 is configured to project so as to be coextensive with at least a portion of the permeate chamber 30. In other words, part of the proximal end 12 of the hollow cylinder 10 may extend into the permeate chamber 30 itself. For example, the permeate chamber 30 may be configured with an opening that is configured to receive the portion of the proximal end 12 which extends away from the distal end 14 and into the permeate chamber 30. Thus, the proximal end 12, in some embodiments, may extend through the permeate chamber 30 so as to reach the retentate chamber 20. For example, the proximal end 12 may extend so as to terminate approximately where the permeate chamber 30 and retentate chamber 20 interface with each other.

When the proximal end 12 terminates in or at the retentate chamber 20, an opening of the proximal end 12 is configured to allow fluid communication between an inside of the hollow cylinder 10 and the permeate chamber 30. In this manner, cell culture media may pass from an interior of the hollow cylinder 10 and may be deposited in the permeate chamber 30. The microATF perfusion filter further includes an inlet 70, positioned over the retentate chamber 20, for communication with a source of positive or negative pressure. For example, the inlet 70 is configured to communicate with a pipette (not shown). The pipette may be inserted into the inlet 70 so as to attach the pipette to the microATF perfusion filter 100. The pipette is used to transport a measured volume of fluid (e.g., cells in cell culture media) by drawing up and dispensing of fluid. For example, the pipette creates a partial vacuum above the retentate chamber 20, which, when released, causes fluid that was previously drawn up to be dispensed.

Further still, the microATF perfusion filter 100 includes an outlet 35, positioned in a wall 32 of the permeate chamber 30. The outlet 35 may be formed as a circular port on the wall 32 of the permeate chamber 30. In some embodiments, the outlet 35 may comprise an opening on the wall 32 of the permeate chamber 30 and a tubular portion which mates with the wall 32. The outlet 35 can be connected to a check valve 40. In particular, the outlet 35 is arranged with the check valve 40 such that the check valve 40 caps the outlet 35. The outlet 35 allows for the removal, if desired, of cell culture media that might be deposited into the permeate chamber 30.

The check valve 40 allows gas to escape from the permeate chamber 30 while allowing no gas to enter. In other words, the check valve 40 is a one-way valve permitting fluid flow in one direction, i.e., from the permeate chamber 30. The check valve 40 is configured to work automatically. In some embodiments, the check valve 40 may be a ball check valve in which a movable part to block fluid flow is a ball which may be spring-loaded to help keep the check valve 40 shut. Further, during the vacuum mode of the pipette, the cells are sucked into hollow fiber filters 60, discussed below in more detail. However, the spent media is not aspirated back into the microATF perfusion filter 100 due to the check valve 40 being connected to the permeate chamber 30. During dispensing, the pipette pushes the cells back down into the lumen of the hollow fiber filters 60, and a portion of the spent media is then transferred into the permeate chamber 30 as the check valve 40 opens.

The check valve 40 can be connected to a hydrophobic fluid vent filter 50. The hydrophobic vent filter 50 does not wet in water, but wets in low surface tension liquids. Once the hydrophobic vent filter 50 becomes wetted, aqueous solutions are permitted to pass through the vent filter 50. For example, moisture in the fluid flowing from permeate chamber 30 through outlet 35 to check valve 40 can in turn be passed through the vent filter 50. The hydrophobic vent filter 50 stops liquid from leaving the microATF perfusion filter 100 once liquid comes in contact with a membrane thereof. The hydrophobic vent filter 50 effectively imparts an actual maximum limit, which can be determined via calculation, on the amount of liquid in the permeate chamber 30. The amount of media taken from the cell culture can then be reintroduced into the bioreactor as fresh media to perform discontinuous perfusion.

Referring again to FIG. 1, the microATF perfusion filter 100 further includes a plurality of hollow fiber filters 60. The hollow fiber filters 60 contain a semi-permeable barrier (i.e., a lumen) in the form of the hollow fibers, through which cell culture media, but not cells, may pass. The hollow fiber filters 60 each have a first end 62 and a second end 64. One or more of the hollow fiber filters 60 are arranged longitudinally inside the hollow cylinder 10 with the second end 64 extending in a direction of the distal end 14 of the hollow cylinder and the first end 62 terminating in or at the retentate chamber 20.

In one embodiment, the hollow fiber filters 60 comprise three hollow fiber filters which are arranged such that a first hollow fiber filter and a second hollow fiber filter are positioned parallel to each other within the hollow cylinder 10 and a third hollow fiber filter is positioned between the first and second hollow fiber filters in a first direction and offset from the first and second hollow fiber filters in a second direction which is orthogonal to the first direction. The hollow fiber filters 60 may be coextensive or partially coextensive with the hollow cylinder 10, such that one of more of the hollow fiber filters 60 is arranged to extend along the length of the hollow cylinder 10 and terminates at or near the distal end 14. In at least one embodiment, the hollow fiber filters 60 may be fixed in place at the distal end 14 and the retentate chamber 20 of the hollow cylinder 10 using adhesive.

In at least one embodiment, the hollow fiber filters 60 of the microATF perfusion filter 100 have an inside diameter ranging from about 0.5 mm to about 1 mm. In at least one embodiment, the hollow fiber filters 60 have an average pore size ranging from about 0.2 µm to about 2.0 µm. More particularly, in at least one embodiment, the one or more hollow fiber filters 60 have an average pore size of about 0.65 µm. Further still, in at least one embodiment, the one or more hollow fiber filters 60 have an average pore size that does not permit passage of molecules having a molecular weight ranging from about 20 kDa to about 70 kDa. More particularly, in at least one embodiment, the one or more hollow fiber filters 60 have an average pore size that does not permit passage of molecules having a molecular weight of about 30 kDa or more. Additionally, in at least one embodiment, the one or more hollow fiber filters 60 have an average pore size that does not permit passage of molecules having a molecular weight of about 50 kDa or more.

In some embodiments, the microATF perfusion filter 100 includes additional components. For example, as shown in FIG. 1, one or more seals 16 are provided at respective interfaces within the microATF perfusion filter. In particular, a first seal 16 is provided between a first portion of the proximal end 12 and the permeate chamber 30, a second seal 16 is provided between the permeate chamber 30 and the retentate chamber 20, and a third seal 16 is provided between the retentate chamber 20 and the inlet 70. The seals 16 act so as to ensure a liquid-tight connection between the respective interfaces and to isolate the contents of the hollow cylinder 10, the permeate chamber 30, the retentate chamber 20 and the inlet 70 from the external environment. The seals 16 may be a flexible membrane that seals and isolates respective components. The seals 16 may comprise elastomer and may further include adhesive.

Figure 2:
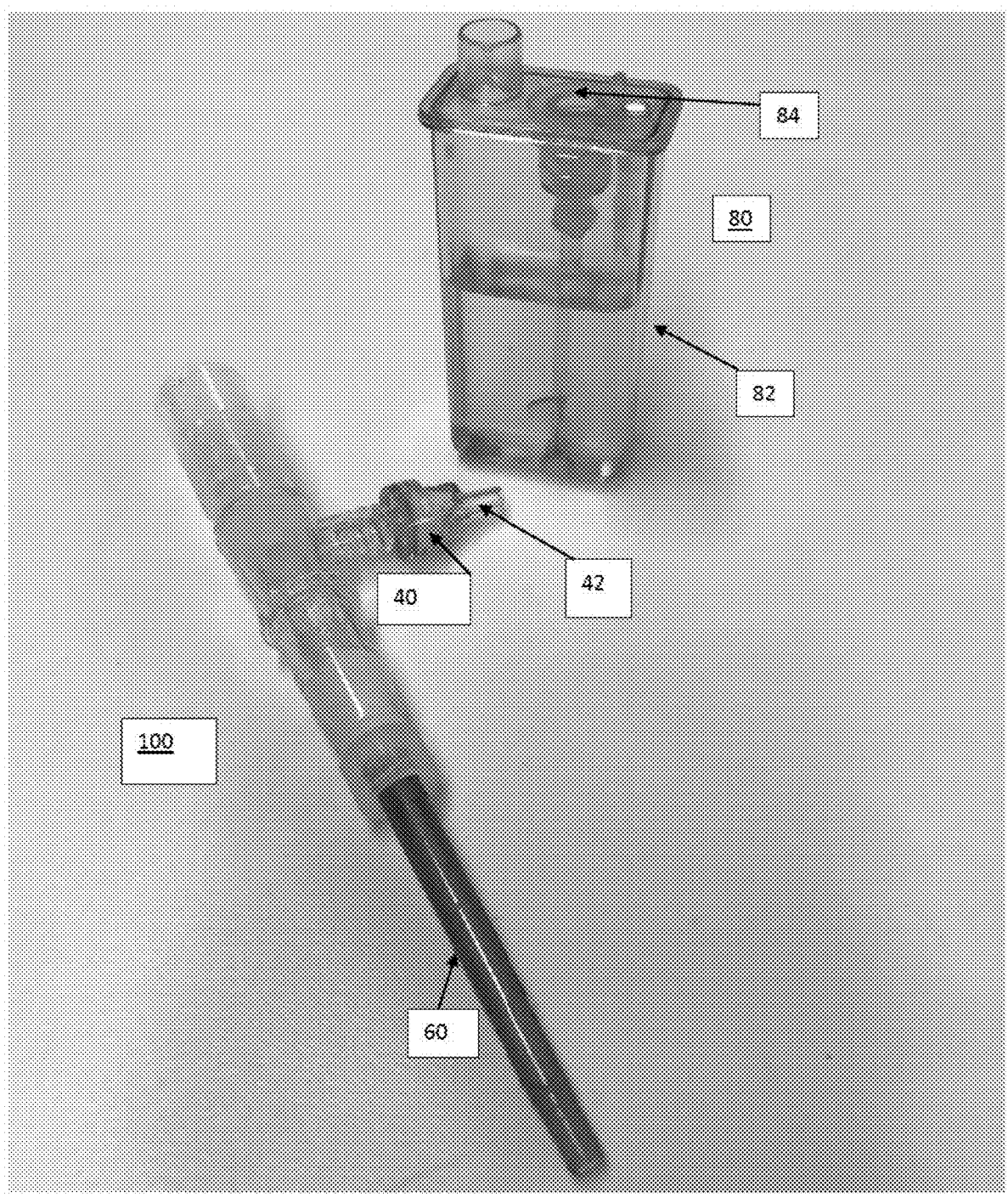
FIG. 2 depicts a system including a process vessel equipped with a perfusion filter according to an exemplary embodiment.

Referring now to FIG. 2, a system including a process vessel and a microATF perfusion filter is shown. More particularly, FIG. 2 depicts a process vessel 80 equipped with a microATF perfusion filter 100. The microATF perfusion filter 100 is configured to extract cells in cell culture media from the process vessel 80. In particular, the hollow cylinder 10 is communicated with the process vessel 80, and pipetting may be used to draw media from the process vessel 80 into the hollow cylinder 10. The micro ATF perfusion filter 100 is not limited to use with the process vessel 80 and may be used with existing commercially available small scale process vessels.

The process vessel 80 comprises a housing 82 capable of holding a volume of cells in cell culture media of about 15 mL or less. In at least one embodiment, the housing 82 holds about 10 mL or less of a volume of cells in cell culture media. More particular, the housing 82 holds about 5 mL or less of a volume of cells in cell culture media. In at least one embodiment, the housing 82 holds about 2 mL or less of a volume of cells in cell culture media. In at least one embodiment, the housing 82 holds about 1 mL or less of a volume of cells in cell culture media. In at least one embodiment, the housing 82 holds about 0.5 mL or less of a volume of cells in cell culture media. In at least one embodiment, the housing 82 holds about 0.2 mL or less of a volume of cells in cell culture media. In at least one embodiment, the volume of cell culture media deposited into the permeate chamber 30 from the process vessel 80 ranges from about 50 µL to about 500 µL. In particular, the volume of cell culture media deposited into the permeate chamber 30 from the process vessel 80 ranges from about 100 µL to about 300 µL.

The housing 82 is communicated, via an opening or a connector 84, with a filter device such as the microATF perfusion filter 100. When the housing 82 is communicated with the microATF perfusion filter 100, at least the distal end 14 of the hollow cylinder 10 is in contact with a volume of cells in cell culture media that can be held in the housing 82. Thus, cells in cell culture media can be withdrawn from the housing 82 into the retentate chamber 20 when the inlet 70 communicates with a source of negative pressure. In contrast, cells in cell culture media are returned to the housing 82, when the inlet 70 communicates with a source of positive pressure.

Under these circumstances, a volume of cell culture media is deposited into the permeate chamber 30. The permeate chamber 30 is communicated with the check valve 40. A conduit 42 may extend from the check valve 40 in a direction away from the wall 32 of the permeate chamber 30. The hydrophobic vent filter 50 (not shown in FIG. 2) may be provided on the conduit 42. The flow from the permeate chamber 30 will stop once fluid from the permeate chamber 30 touches the hydrophobic vent filter 50 downstream from the check valve 40, ensuring that a precise volume of fluid is removed.

The source of positive or negative pressure is provided through a pipette (not shown). For example, the source of the negative pressure is the vacuum established by the pipette when the pipette is moved in a first direction, and the source of the positive pressure is the pipette when the pipette is moved in a second direction that is opposite to the first direction. The source of positive or negative pressure is provided through a pipette operated manually or robotically. The pipette may be a "single hand" pipette or a multi-hand pipette.

In particular, a robotic controller may be used to operate the pipette automatically, so as to control extraction of cells in cell culture media from the process vessel 80 by the microATF perfusion filter 100. The robotic controller may include one or more controllers programmed to control the positive and negative air source, by regulating operation of the pipette. Further, the controller 5 may adjust operations of the pipette in order to satisfy a process requirement. In at least one embodiment, the robotic controller may be a controller provided with the Ambr®15 cell culture process vessel system made by Sartorius Stedim Biotech Group, Royston, Hertfordshire, UK. The controller may be programmed to carry out liquid transfer at microscale amounts, in accordance with instructions executed by a processor of the controller.

The robotic controller may include a processor or microprocessor configured to run an operating system, an application-specific integrated circuit (ASIC), a field-programmable gate array (FPGA), etc., or combinations thereof. The controller may include memory which may include, but is not limited to, electronic, optical, magnetic, or any other storage or transmission device capable of providing a processor, ASIC, FPGA, etc. with program instructions. The memory may include a memory chip, Electrically Erasable Programmable Read-Only Memory (EEPROM), erasable programmable read only memory (EPROM), flash memory, or any other suitable memory from which the controller can read instructions. The instructions may include code from any suitable programming language.

Further, in certain embodiments, a user interface is provided where users can control and/or monitor various facets of the pipette, the process vessel 80, and the microATF perfusion filter 100. The user interface may also display other data stored in the memory of controller 5, including data relating to the operation of the pipette and microATF perfusion filter 100, respectively, at each of a plurality of points in time.

The robotic pipette system may include at least one communications unit that may be coupled to a switch and a router for providing a communication link between the system and a network. As such, the communications unit enables the processor to communicate, wired or wirelessly, with other electronic systems coupled to the network. For instance, the communications unit may be coupled to an Ethernet line that connects the system to the Internet or another network. In other implementations, the communications unit may be coupled to an antenna (not shown) and provides functionality to transmit and receive information over a wireless communication interface with the network.

In various implementations, the communications unit may include one or more transceivers configured to perform data communications in accordance with one or more communications protocols including but not limited to WLAN protocols (e.g., IEEE 802.11 a/b/g/n/ac/ad, IEEE 802.16, IEEE 802.20, etc.).

Certain embodiments of the robotic system may be practiced in a networked environment using logical connections to one or more remote computers having processors. Persons skilled in the art will appreciate that such network computing environments may encompass many types of computers, including personal computers, hand-held devices, multiprocessor systems, microprocessor-based or programmable consumer electronics, network PCs, minicomputers, mainframe computers, and so on. Implementations may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Figure 3:
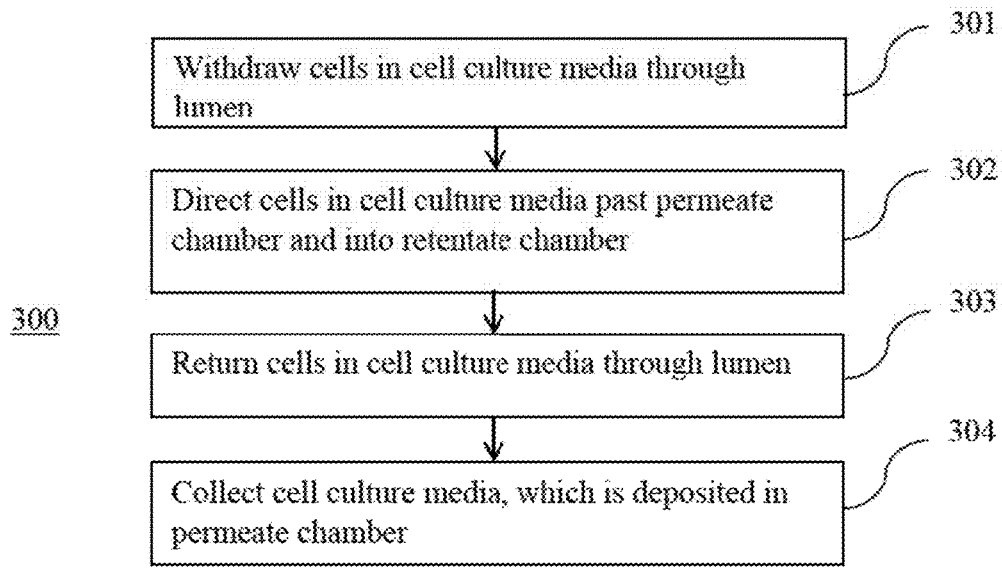
FIG. 3 depicts a method according to an exemplary embodiment.

FIG. 3 depicts a method of conducting a discontinuous perfusion of cells in cell culture media across an alternating tangential flow perfusion filter, according to an exemplary embodiment. Specifically, FIG. 3 depicts a method 300 as may be carried out using the microATF perfusion filter 100 described above. The method 300 comprises withdrawing cells in cell culture media (step 301). The cells may range in volume from about 0.5 mL to about 5 mL. Withdrawing the cells comprises filtering the cells through a lumen of one or more hollow fiber filters 60. The cells are filtered through the hollow fiber filters 60 and directed past a permeate chamber 30 and into a retentate chamber 20 (step 302). The method further comprises returning the cells in cell culture media through the lumen of said one or more hollow fiber filters 60 (step 303). In returning the cells through the lumen, the volume of cell culture media passes across a porous wall of said one or more hollow fiber filters 60 and collects in the permeate chamber 30 (step 304).

In at least one embodiment, the method may be implemented in a system including the process vessel 80 equipped with the microATF perfusion filter 100. In particular, perfusion may be performed to maintain the process vessel 80 such that equivalent volumes of media are added and removed from the process vessel 80 while cells are retained in the process vessel 80. Thus, a steady source of fresh nutrients and efficient removal of waste products may be carried out. In at least one embodiment, perfusion may be performed discontinuously, e.g., at predetermined intervals.

In at least one embodiment, the method 300 is carried out such that the volume of cell culture media which collects in the permeate chamber 30 ranges from about 25 µL to about 1000 µL. In at least one embodiment in which discontinuous perfusion is performed, the volume of cell culture media, which collects in said permeate chamber, ranges from about 0.1 mL to about 0.5 mL.

Figure 4:
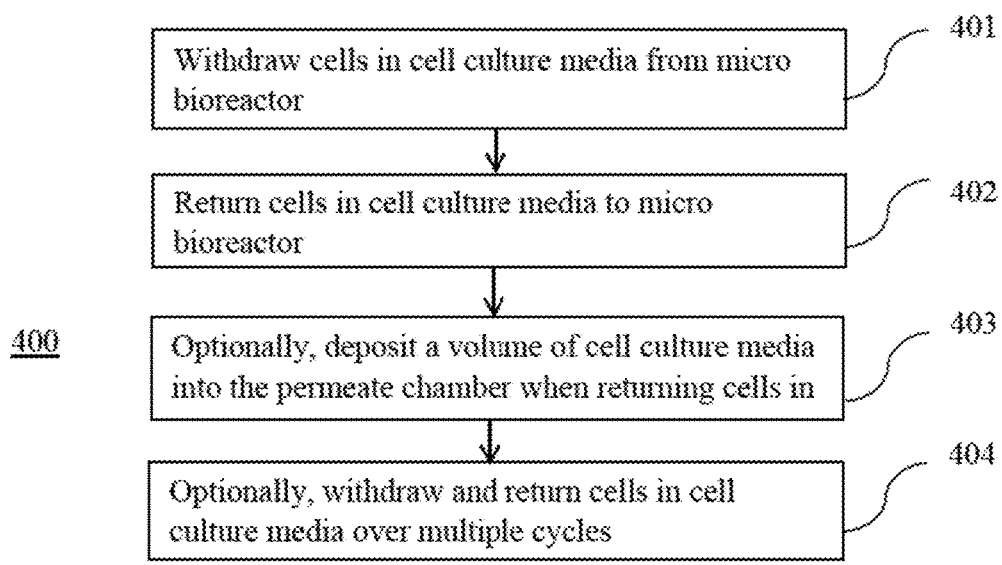
FIG. 4 depicts a method according to an exemplary embodiment.

FIG. 4 depicts a method according to an exemplary embodiment. In particular, FIG. 4 depicts a method 400 of perfusing cells in cell culture media held in a process vessel. The process vessel may be the process vessel 80, for example, and may hold no more than about 15 mL of cells in cell culture media. The method 400 includes withdrawing cells in cell culture media from the process vessel 80 (step 401). As mentioned above, the process vessel 80 includes a housing 82 holding the cells in cell culture media. The cells may be withdrawn from the housing 82 using a micro alternating tangential flow perfusion filter, such as the microATF perfusion filter 100 described above. The method 400 may further include directing the cells through hollow fiber filters. Additionally, the method includes returning at least a portion of the cells in cell culture media to the process vessel (step 402). The method 400 may optionally include additional steps, as described below.

In at least one embodiment, the method 400 further includes depositing a volume of cell culture media into the permeate chamber 30 when returning the cells in cell culture media to the process vessel 80 (step 403). Further still, in at least one embodiment, cells in cell culture media withdrawn from the process vessel 80 may range in volume from about 0.5 mL to about 5 mL. In at least one embodiment, the cells in cell culture media withdrawn from the process vessel 80 range in volume from about 1.0 mL to about 3.0 mL, and more specifically, may amount to about 2.0 mL in volume. Additionally, in at least one embodiment, the volume of cell culture media, which is deposited into the permeate chamber 30, ranges from about 10 µL to about 300 µL. Further, in at least one embodiment, the volume of cell culture media, which is deposited into the permeate chamber 30 ranges from about 50 µL to about 250 µL, and more particularly, from about 100 µL to about 200 µL.

Further still, according to certain embodiments, perfusion may be carried out over multiple cycles of alternating tangential flow of the cells in cell culture media through one or more hollow fiber filters such as the hollow fiber filters 60 shown in FIGS. 1-2 (step 404). In particular, cells in cell culture media are withdrawn and returned over multiple cycles of alternating tangential flow of the cells over a porous wall of said one or more hollow fiber filters. The withdrawal and return of cells in cell culture media over multiple cycles of alternating tangential flow are repeated intermittently. For example, the withdrawal and return of cells may be carried out every half hour or every hour. When the robotic controller is used to control pipetting from the microATF perfusion filter 100, an input to the controller may be used to establish the timing of the cell withdrawal and return.

Further, the method 400 may further include introducing fresh cell culture media to the process vessel. In at least one embodiment, the fresh cell culture media introduced amounts to approximately the volume of cell culture media, which is deposited into the permeate chamber 30 over said multiple cycles of alternating tangential flow. In at least one embodiment, about 1 mL to about 3 mL of fresh cell culture media is introduced to the process vessel 80. Further, in at least one embodiment, about 1.5 mL to about 2.5 mL of fresh cell culture media is introduced, and more particularly, approximately 2 mL of fresh cell culture media is introduced.

Figure 5A:
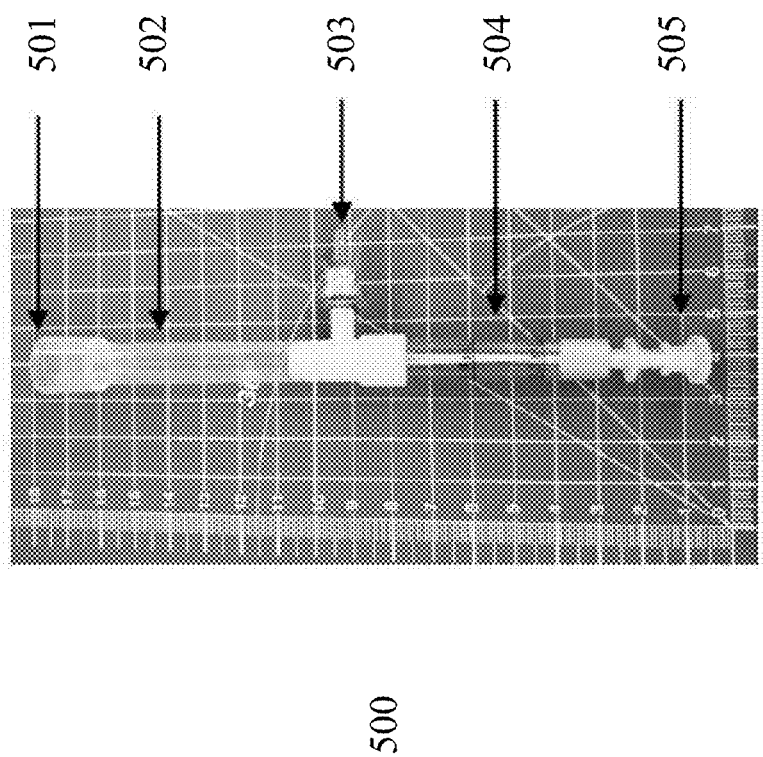
FIG. 5a depicts a micro alternating tangential flow (microATF) perfusion filter device according to an exemplary embodiment.

FIG. 5a depicts a micro alternating tangential flow (microATF) perfusion filter device 500 in an exemplary embodiment. The microATF perfusion filter 500 includes an attachment point 501 for a robot, pipetter or other source of alternating positive and negative pressure, and an optional pipette tip 502 for such robot, pipetter, etc. The microATF 500 further comprises a filter housing 504 in fluid communication with the attachment point 501 (e.g., by means of the optional pipette tip 502). Within the filter housing 504 is a filter element (not shown), separating at least a portion of the filter housing 504 into feed/retentate and permeate chambers. A microATF tip 505 is disposed at a second end of the housing in fluid communication with the feed/retentate chamber, and provides a means for fluid communication (e.g., via tubing or other suitable conduit) with a process vessel according to this disclosure. A permeate outlet 503 comprising a one-way or check-valve is integrated into or connected to the permeate chamber; the check valve serves to prevent backflow across the filter element during the negative pressure portion of an alternating pressure cycle.

Figure 5B:
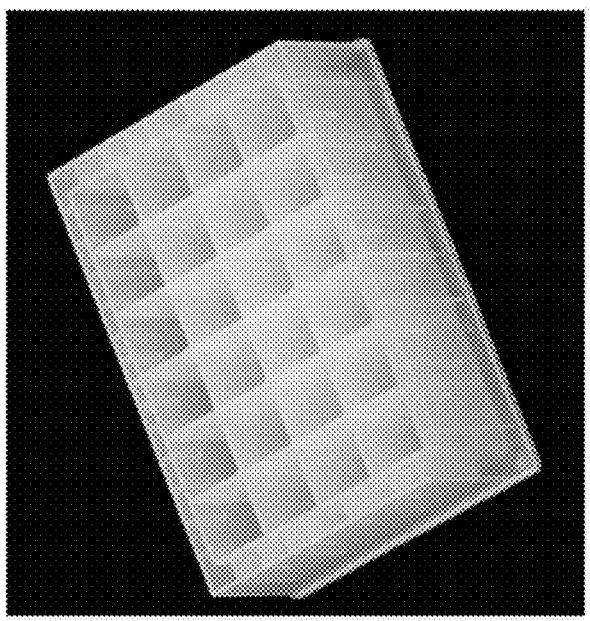
FIG. 5b depicts a multi-well plate according to an exemplary embodiment.

FIG. 5b depicts an embodiment of a process vessel 506 comprising a multi-well plate. Process vessel 506 may be used in a system or method with a microATF as described above (e.g., the microATF depicted in FIG. 5a). In use, each of the plurality of wells of the process vessel 506 may be fluidly connected to separate microATFs to permit parallel perfusion culture and/or harvest from multiple systems simultaneously.

The process vessels and microATFs described above have a number of useful or advantageous features which will be evident to those of skill in the art. As one non-limiting example, the microATF filters described herein are capable of effectively filtering volumes of 1 ml or less (e.g., 200 µl, 500 µl, etc.). These low volumes are conducive to use in parallel and/or large-scale applications such as screening of therapeutics, and the development, optimization and/or validation of filtration systems and methods. MicroATF systems of this disclosure may be implemented in arrays, similar to the arrays currently utilized for fluid handling in automated cell culture systems such as the AMBR™ parallel bioreactor (Sartorius AG, Gottingen, Germany) or multi-channel pipettors such as the eppendorf epMotion® devices (eppendorf AG, Hamburg, Germany).

Various alternative embodiments are contemplated and form part of this disclosure. For example, in one embodiment, the hollow fiber filters 60 are not provided in a hollow cylinder 10, but are open in the microATF device and adhered using adhesive at the inlet 70 and retentate chamber 20. Further, in one or more embodiments, the permeate chamber 30 and/or retentate chamber 20 may be omitted.

While this specification contains specific implementation details, these should not be construed as limitations on the scope of what may be claimed, but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, the separation of various system components in the implementations described above should not be understood as requiring such separation in all implementations, and it should be understood that the described components and systems can generally be integrated in a single product or packaged into multiple products.

As utilized herein, the terms "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure.

The terms "coupled," "connected," and the like as used herein mean the joining of two components directly or indirectly to one another. Such joining may be stationary (e.g., permanent) or moveable (e.g., removable or releasable). Such joining may be achieved with the two components or the two components and any additional intermediate components being integrally formed as a single unitary body with one another or with the two components or the two components and any additional intermediate components being attached to one another.

The terms "fluidly coupled," "in fluid communication," and the like as used herein mean the two components or objects have a pathway formed between the two components or objects in which a fluid, such as water, air, biological fluid, etc., may flow, either with or without intervening components or objects. Examples of fluid couplings or configurations for enabling fluid communication may include piping, channels, or any other suitable components for enabling the flow of a fluid from one component or object to another.

It is important to note that the construction and arrangement of the system shown in the various exemplary implementations are illustrative only and not restrictive in character. All changes and modifications that come within the spirit and/or scope of the described implementations are desired to be protected. It should be understood that some features may not be necessary and implementations lacking the various features may be contemplated as within the scope of the application, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A method of discontinuously perfusing cells in cell culture media across a micro alternating tangential flow perfusion device (microATF device) comprising:
withdrawing a volume from about 0.5 mL to about 5 mL of cells in cell culture media from a process vessel having a capacity of no more than about 15 mL through a lumen of one or more hollow fiber filters into a retentate chamber of said microATF device, wherein a distal filter housing portion of said microATF device is in direct contact with the cell culture media in said process vessel; and
returning said cells in cell culture media through the lumen of said one or more hollow fiber filters,
thereby filtering a volume of cell culture media across a porous wall of said one or more hollow fiber filters into a permeate chamber of said microATF device, said permeate chamber comprising an outlet that is capped with a check valve which prevents backflow into the lumen of the hollow fiber filters, and
wherein said withdrawing and said returning is accomplished by generating alternating positive and negative pressure with a pipette.

2. The method of claim 1 in which the volume of cell culture media, which collects in said permeate chamber, ranges from about 25 µL to about 1000 µL.

3. The method of claim 1 in which the cells in cell culture media withdrawn from the process vessel amount to about 2.0 mL in volume.

4. The method of claim 2 in which the volume of cell culture media, which is deposited into the permeate chamber, ranges from about 10 µL to about 300 µL.

5. The method of claim 1 in which the cells in cell culture media are withdrawn and returned over multiple cycles of alternating tangential flow of cells in cell culture media over a porous wall of said one or more hollow fiber filters.

6. The method of claim 5 in which the withdrawal and return of cells in cell culture media over multiple cycles of alternating tangential flow are repeated intermittently.

7. The method of claim 5 which further comprises introducing fresh cell culture media to the process vessel.

8. The method of claim 5 in which the withdrawal and return of cells in cell culture media over multiple cycles of alternating tangential flow are under a pressure of about 1 psi.

9. The method of claim 7 in which the fresh cell culture media introduced amounts to approximately the volume of cell culture media deposited into the permeate chamber over said multiple cycles of alternating tangential flow.

10. The method of claim 9 in which about 1 mL to about 3 mL of fresh cell culture media is introduced.

11. The method of claim 9 in which approximately 2 mL of fresh cell culture media is introduced.

12. A method of harvesting a cell product from a cell culture, the method comprising:
(a) culturing cells in a starting volume of 15 ml or less of culture media until the cells have produced a cell product in the culture media, wherein the cells are cultured in a cell culture system comprising a process vessel having a culture capacity of no more than 15 mL, said process vessel releasably connected to a micro-alternating tangential flow (microATF) device, wherein a housing portion of said microATF device is in direct contact with culture media in said process vessel;
(b) transferring the culture media between the process vessel and the microATF device by generating alternating positive and negative pressure with a pipette and thereby causing the cell product to pass through the one or more hollow fiber filters of the microATF device and into a permeate chamber; and
(c) recovering the cell product from the permeate chamber.

13. The method of claim 12, further comprising the steps of:
refilling the process vessel with a desired volume of culture media; and repeating at least steps (b) and (c) of the method.

14. The method of claim 12, wherein the process vessel is a multi-well plate.

15. The method of claim 14, wherein the starting volume is 0.2, 0.5, 1.0, 1.5, or 2.0 mL.

16. The method of claim 14, wherein a plurality of fluid conduits connect a plurality of wells of the multi-well plate with a plurality of microATF devices.

* * * * *